United States Patent
Ikeda et al.

(10) Patent No.: US 9,713,441 B2
(45) Date of Patent: Jul. 25, 2017

(54) OPTICAL ROTATION MEASUREMENT METHOD AND OPTICAL ROTATION MEASUREMENT APPARATUS

(71) Applicant: SEIKO EPSON CORPORATION, Tokyo (JP)

(72) Inventors: Akira Ikeda, Nagano (JP); Kazuhiro Nishida, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 243 days.

(21) Appl. No.: 14/604,115

(22) Filed: Jan. 23, 2015

(65) Prior Publication Data

US 2015/0216453 A1    Aug. 6, 2015

(30) Foreign Application Priority Data

Jan. 31, 2014  (JP) ................................. 2014-017020

(51) Int. Cl.
- *A61B 5/1455* (2006.01)
- *A61B 5/145* (2006.01)
- *A61B 5/00* (2006.01)

(52) U.S. Cl.
CPC ........ *A61B 5/1455* (2013.01); *A61B 5/14532* (2013.01); *A61B 5/6816* (2013.01); *A61B 5/6826* (2013.01)

(58) Field of Classification Search
CPC .............. A61B 5/1455; A61B 5/14532; A61B 5/14558
See application file for complete search history.

(56) References Cited

U.S. PATENT DOCUMENTS

| | | | | |
|---|---|---|---|---|
| 4,704,029 A | * | 11/1987 | Van Heuvelen ... | A61B 5/14558 600/316 |
| 6,208,415 B1 | * | 3/2001 | De Boer ............ | G01B 9/02011 356/450 |
| 6,594,510 B2 | * | 7/2003 | Madarasz .......... | A61B 5/14558 600/316 |
| 6,725,073 B1 | * | 4/2004 | Motamedi .......... | A61B 5/14532 600/316 |
| 6,775,007 B2 | * | 8/2004 | Izatt ..................... | A61B 5/0066 356/479 |
| 8,842,277 B2 | | 9/2014 | Goto et al. | |
| 8,908,189 B2 | * | 12/2014 | Tumlinson ......... | G01B 9/02011 356/479 |
| 2013/0033707 A1 | | 2/2013 | Yamada et al. | |

FOREIGN PATENT DOCUMENTS

| JP | 2004-113434 A | 4/2004 |
|---|---|---|
| JP | 3966796 B2 | 8/2007 |
| JP | 2008-309707 A | 12/2008 |
| JP | 5078004 B2 | 11/2012 |
| JP | 2013-036792 A | 2/2013 |
| JP | 2013-156143 A | 8/2013 |
| JP | 2014-130045 A | 7/2014 |
| JP | 2014-130046 A | 7/2014 |

\* cited by examiner

*Primary Examiner* — Eric Winakur
(74) *Attorney, Agent, or Firm* — Global IP Counselors, LLP

(57) ABSTRACT

An optical rotation measurement method includes causing measurement light of a predetermined polarization to be incident on a subject from an incident direction that is a non-right angle to the subject, discriminating an optical rotation reflecting component of the predetermined polarization from reflected light that is reflected in a different direction to the incident direction of the subject, and measuring the optical rotation based on the discrimination result.

9 Claims, 5 Drawing Sheets

OPTICAL ROTATION MEASUREMENT METHOD AND OPTICAL ROTATION MEASUREMENT APPARATUS

This application claims the benefit of Japanese Patent Application No. 2014-017020, filed on Jan. 31, 2014.

The content of the aforementioned application is incorporated herein by reference in its entirety.

BACKGROUND

1. Technical Field

The present invention relates to an optical rotation measurement method for measuring optical rotation, and the like.

2. Related Art

The components of a substance can be known by utilizing properties such as the absorption, scattering and optical rotation of light by the substance, without directly contacting the substance. For example, measuring optical rotation enables the density of a substance to be estimated (calculated). Optical rotation is a property according to which the polarization plane rotates when linear polarized light passes through an optically active substance such as glucose, for example. Another known technology involves, for example, measuring the components of a living body by irradiating the living body with near-infrared light and acquiring the spectral characteristics of scattered light and transmitted light from reflected light that is received (refer to JP-A-2008-309707).

Generally, reflective optical measurement is performed by causing measurement light to be incident perpendicularly on the surface of a subject and receiving the reflected light such as with the technology of JP-A-2008-309707. However, it is considered difficult to measure optical rotation with a configuration that measures reflected light that is reflected in the same direction as the incident direction. This is because the optical rotation that occurs in the process of light being propagated in the incident direction is cancelled out in the process of the reflected light being propagated in the opposite direction to the incident direction.

SUMMARY

An advantage of some aspects of the invention is to measure optical rotation accurately, while suppressing a situation in which optical rotation is cancelled out due to reflected light being reflected in the same direction as the incident direction of measurement light.

A first aspect of the invention is an optical rotation measurement method that includes causing a measurement light of a predetermined polarization to be incident on a subject from an incident direction that is a non-right angle to the subject, discriminating an optical rotation reflecting component of the predetermined polarization from a reflected light that is reflected in a different direction to the incident direction of the subject, and measuring an optical rotation based on a result of the discrimination.

Also, a fifth aspect of the invention is an optical rotation measurement apparatus including a measurement light irradiation unit that causes a measurement light of a predetermined polarization to be incident on a subject from an incident direction that is a non-right angle to the subject, a discrimination unit that discriminates an optical rotation reflecting component of the predetermined polarization from a reflected light that is reflected in a different direction to the incident direction of the subject, and a measurement unit that measures an optical rotation based on a result of the discrimination.

According to the first and fifth aspects of the invention, optical rotation can be measured by causing measurement light of predetermined polarization to be incident on a subject from an incident direction that is a non-right angle to the subject, and discriminating the optical rotation reflecting component of the predetermined polarization from reflected light that is from a different direction to the incident direction of the measurement light. Accordingly, optical rotation can be accurately measured, while suppressing a situation in which optical rotation is cancelled out due to reflected light being reflected in the same direction as the incident direction of measurement light.

A second aspect of the invention is the optical rotation measurement method according to the first aspect that further includes obtaining the measurement light and a reference light from a linear polarized light, and causing the reference light to combine and interfere with the reflected light, and in which the discrimination includes performing the discrimination using a result of the interference.

Also, a sixth aspect of the invention is the optical rotation measurement apparatus according to the first aspect that further includes a splitting unit that splits a linear polarized light into the measurement light and a reference light, and a combining unit that causes the reference light to combine and interfere with the reflected light, and in which the discrimination unit discriminates the optical rotation reflecting component using a result of the interference.

According to the second and sixth aspects of the invention, a reference light can be caused to interfere with the polarized light component of measurement light in reflected light. Accordingly, it is possible to discriminate the optical rotation reflecting component in reflected light in a simple manner, thus enabling optical rotation to be easily measured.

A third aspect of the invention is the optical rotation measurement method of the second aspect that further includes changing a light path length of the reference light up to where the reference light is combined with the reflected light.

Also, a seventh aspect of the invention is the optical rotation measurement apparatus of the sixth aspect that further includes a light path length changing mechanism that changes a light path length of the reference light up to where the reference light is combined with the reflected light.

According to the third and seventh aspects of the invention, the light path length of a reference light up until the point at which the reference light is combined with reflected light can be changed.

A fourth aspect of the invention is the optical rotation measurement method of the third invention in which the measurement includes measuring the optical rotation using the light path length.

Also, an eighth aspect of the invention is the optical rotation measurement apparatus of the seventh invention in which the measurement unit measures the optical rotation using the light path length.

According to the fourth and eighth aspects of the invention, optical rotation can be measured using the light path length of a reference light up until the point at which the reference light is combined with reflected light.

A ninth aspect of the invention is the optical rotation measurement apparatus of any of the sixth to eighth aspects of the invention in which the splitting unit and the combining unit are configured to share a single beam splitter.

According to the ninth aspect of the invention, the splitting unit and the combined part can be constituted to share a single beam splitter.

A tenth aspect of the invention is the optical rotation measurement apparatus of any of the fifth to ninth aspects of the invention in which the measurement light irradiation unit includes a lens unit that serves as an optical front end unit through which incoming and outgoing light passes to and from the subject, causes the measurement light to be incident on the subject from an incident direction that is a non-right angle to the subject, by shifting an optical axis of the measurement light that passes through the lens unit from a principal point of the lens unit, and is configured such that the reflected light passes through a position that is symmetrical to the optical axis of the measurement light with the principal point of the lens unit interposed therebetween.

According to the tenth aspect of the invention, a lens unit is used to cause measurement light to be incident on a subject from an incident direction that is a non-right angle to the subject, and to collect reflected light from a different direction to the incident direction.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, a configuration for implementing an optical rotation measurement method and an optical rotation measurement apparatus of the invention will be described, with reference to the drawings. This embodiment is incorporated for use in a configuration for measuring the optical rotation of an optically active substance such as glucose, such as a device for measuring a person's blood sugar level (blood sugar level measurement apparatus), for example. In the present embodiment, a blood sugar level measurement apparatus to which an optical rotation measurement apparatus is applied will be illustrated. Note that the invention is not limited by the embodiments that will be described below, and the configuration to which the invention is applicable is not limited to the following embodiments. Also, in the description of the drawings, the same reference signs are given to like portions.

Overall Configuration

Figure 1:
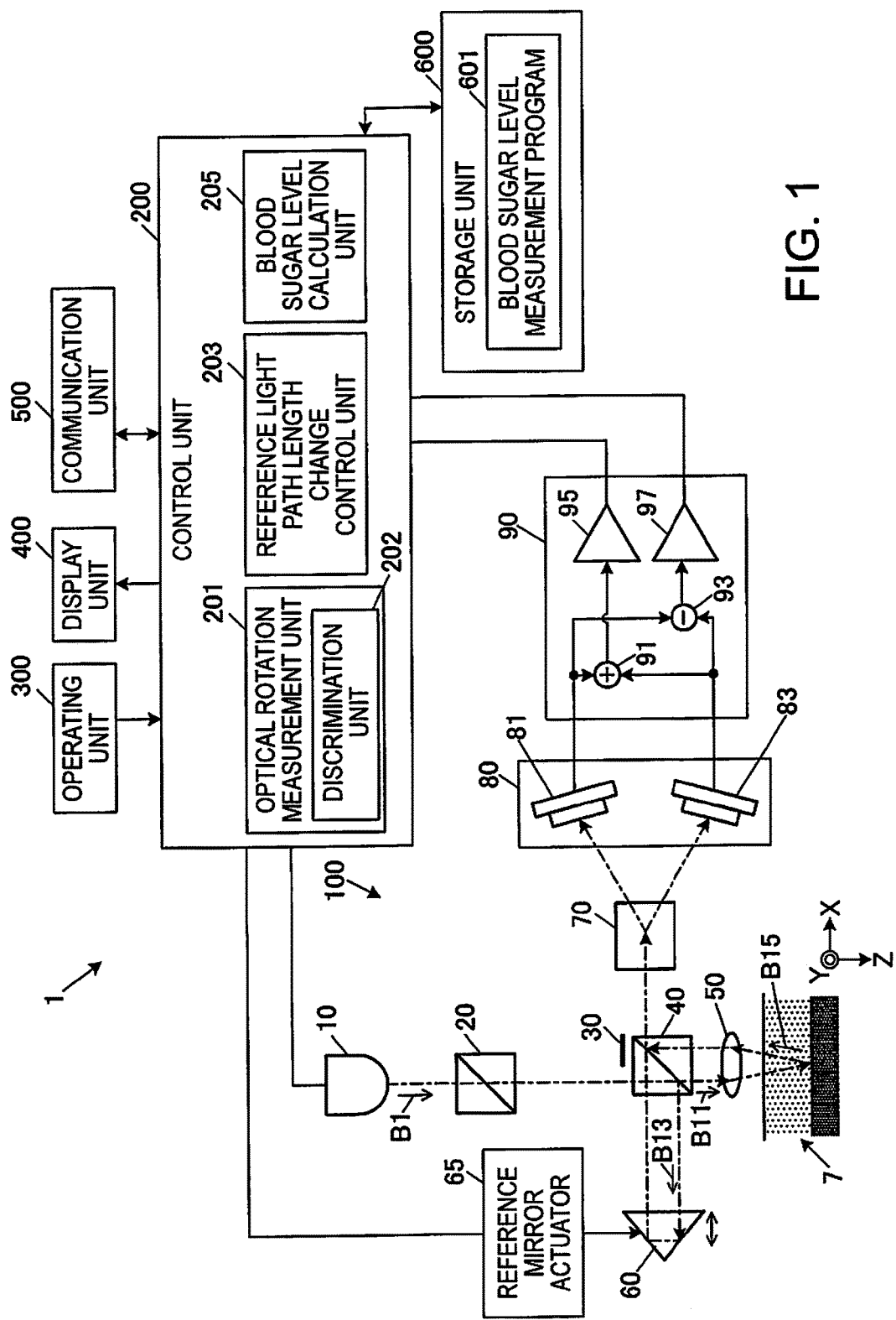
FIG. 1 is a block diagram showing an exemplary overall configuration of a blood sugar level measurement apparatus.

FIG. 1 is a block diagram showing an exemplary overall configuration of a blood sugar level measurement apparatus 1 in the embodiment. This blood sugar level measurement apparatus 1 measures the optical rotation of glucose with a living body such as an earlobe, a fingertip or the epidermis of a finger of the person being measured as a subject 7. The blood sugar level is calculated based on the optical rotation measurement result.

As shown in FIG. 1, the blood sugar level measurement apparatus 1 is mainly configured by an optical device 100, a control unit 200, an operating unit 300, a display unit 400, a communication unit 500, and a storage unit 600.

The optical device 100 is provided with a light source 10, a linear polarizer 20, a beam splitter 40, a condenser lens 50, a reference mirror 60, an orthogonal separation unit 70, a light receiving unit 80, and an amplification unit 90. Optical elements constituting the constituent members from the linear polarizer 20 to the light receiving unit 80 are disposed in appropriate locations along the light path that is shown by the dashed-dotted line in FIG. 1 of irradiated light B1 emitted from the light source 10. Also, the optical device 100 is provided with a shutter 30 disposed upstream of the beam splitter 40 in proximity thereto.

In this optical device 100, the light source 10, the linear polarizer 20, the beam splitter 40 and the condenser lens 50 function as a measurement light irradiation unit. Also, the beam splitter 40 functions as a splitting unit and a combining unit. Also, the condenser lens 50 corresponds to a lens unit, and a reference mirror actuator 65 corresponds to a light path length changing mechanism. Here, the emission direction of the irradiated light B1 from the light source 10 is defined as the Z direction, and a plane that is perpendicular to the Z-axis direction is defined as an XY plane (plane substantially parallel to the skin surface of the living body serving as the subject 7 and orthogonal to the Z-axis direction).

The light source 10 emits the irradiated light B1 of a predetermined wavelength that realizes a low coherence light source. Here, in the case where the subject is a living body, a light having a center wavelength $\lambda$ of 900 nm to 1300 nm is suitable for measurement. This is because a living body is a scattering body, and light will not penetrate into the living body due to scattering in a wavelength band where $\lambda$ is less than 900 nm, and will be absorbed by the water occupying approximately 60% of the living body when $\lambda$ exceeds 1300 nm.

Also, in the present embodiment, the distance that the measurement light B11 penetrates into the living body (depth l of position at which the measurement light B11 is reflected; refer to FIG. 2) which will be discussed later is variably controlled, in order to discriminate the component that reflects the optical rotation of reflected light B15 (hereinafter, "optical rotation reflecting component") utilizing the interference phenomenon of light. An interference distance $\Delta l$, which is the difference between the light path length of the measurement light B11 and the light path length of the reference light B13 that are caused to interfere with each other for this purpose, is equal to the resolution in the depth direction. Accordingly, in order to perform measurement with high accuracy, it is favorable to use a light source with a short interference distance $\Delta l$ of 100 μm or less, such as a light source used in a common OCT (Optical Coherence Tomography) system.

Specifically, a SLED (Superluminescent Diode) can be used. For example, in the case of using a commercial SLED having a center wavelength $\lambda$ of 1050 nm and a bandwidth $\Delta \lambda$ of 60 nm, the interference distance $\Delta l$ that is derived with the following equation (1) is 8.1 μm, and is suitable for measurement. Note that the light source is not limited to a SLED, and any light source having an interference distance of 100 μm or less in a wavelength of 900 nm to 1300 nm can be similarly used.

$$\Delta l = \frac{2\ln 2}{\pi} \cdot \frac{\lambda^2}{\Delta \lambda} \qquad (1)$$

The linear polarizer 20 converts the irradiated light B1 from the light source 10 into linear polarized light. The subsequent measurement light B11 and the subsequent reference light B13 will thereby both be linear polarized light (predetermined polarized light). This linear polarizer 20 is constituted by, for example, a Glan-Thompson prism, which is a type of Glan polarizer, or the like.

The shutter 30 is formed by a light blocking material, and causes the irradiated light B1 that has passed through the linear polarizer 20 to be incident on the left side (as viewed facing FIG. 1) of the beam splitter 40 by shading the right half (as viewed facing FIG. 1) of the beam splitter 40. Here, the beam splitter 40 and the downstream condenser lens 50 are disposed such that the respective centers thereof are shifted to the right side relative to the optical axis of the measurement light B11 (irradiated light B1), and the measurement light B11 transmitted through the left side of the beam splitter 40 is incident on a measurement light incident position P11 shifted to the left side from a principal point P1 of the condenser lens 50 shown in FIG. 2.

The beam splitter 40 causes the light path of the irradiated light (linear polarized light) B1 that is incident on the left side thereof from above after passing through the linear polarizer 20 to diverge and be split into transmitted light and reflected light (functions as a splitting unit). The transmitted light is guided to the condenser lens 50 as the measurement light B11, and reflected light is guided to the reference mirror 60 as the reference light B13. Also, the beam splitter 40 causes the reference light B13 that is reflected by the reference mirror 60 to combine and interfere with the reflected light B15 that is incident on the right side thereof from below via the condenser lens 50 after being reflected inside the subject 7 as will be discussed later, and be incident on the orthogonal separation unit 70 (functions as a combining unit). As will be discussed later in detail, the optical rotation reflecting component that reflects the optical rotation of the original linear polarized light is discriminated by causing the reference light B13 to interfere with the reflected light B15 to thereby enhance the optical rotation reflecting component.

The condenser lens 50 causes the measurement light B11 that is incident on the measurement light incident position P11 to refract and be incident on the surface (skin surface) of the subject 7 at a non-right angle (at an incline). Also, as shown in FIG. 2, the condenser lens 50 condenses the reflected light B15 from the subject 7 at a reflected light incident position P13 on the opposite side (right side) to the measurement light incident position P11 with the principal point P1 interposed therebetween, and causes the condensed light to be incident on the right side of the beam splitter 40 that is shaded from the irradiated light B1 being incident thereon. The measurement light incident position P11 and the reflected light incident position P13 are symmetrically positioned with the principal point P1 interposed therebetween. The condenser lens 50 thus functions as an optical front-end unit and allows incoming and outgoing light to and from the subject 7 to pass.

The reference mirror 60 reflects the reference light B13 from the beam splitter 40, and causes the reference light B13 to again be incident on the beam splitter 40. This reference mirror 60 is configured to be movable within a predetermined range of movement along the optical axis of the reference light B13 (X-axis direction) by the reference mirror actuator 65, which is a motor or the like. Here, in the present embodiment, the irradiated light B1 is incident on the beam splitter 40 from the upper left side, and the reflected light B15 is incident on the beam splitter 40 from the lower right side, with neither incident direction being on the same axis. Thus, the reference mirror 60 preferably is configured by a prism mirror, a corner cube prism or the like that shifts in parallel with the optical axis of the reference light B13 and reflects the reference light B13. The reference light B13 can thereby be reliably caused to combine and interfere with the reflected light B15 in the beam splitter 40.

The orthogonal separation unit 70 separates the reflected light B15 from the beam splitter 40 after interference with the reference light B13 into polarized light components P and S that differ by 90 degrees to each other. This orthogonal separation unit 70 is constituted by a Wollaston prism, a polarized light beam splitter or the like, for example.

The light receiving unit 80 is for receiving the P component and S component separated by the orthogonal separation unit 70, and is provided with a P polarized light receiving unit 81 for receiving the P component and an S polarized light receiving unit 83 for receiving the S component. The P polarized light receiving unit 81 photoelectrically converts the received P component and outputs a voltage value that depends on the amount of received light to the amplification unit 90. The S polarized light receiving unit 83 photoelectrically converts the received S component and outputs a voltage value that depends on the amount of received light to the amplification unit 90. The P polarized light receiving unit 81 and the S polarized light receiving unit 83 are constituted by light detectors such as photodiodes.

The amplification unit 90 is an operation unit that amplifies the difference and the sum of the light reception levels of the P component and the S component received by the light receiving unit 80, and is provided with an adder 91, a subtracter 93, an amplifier 95 for use in addition, and an amplifier 97 for use in subtraction. The output from the P polarized light receiving unit 81 and the S polarized light receiving unit 83 is added by the adder 91 and subtracted by the subtracter 93, and the resultant values are respectively amplified by the amplifier 95 for addition and the amplifier 97 for subtraction. The amplifier 95 for addition outputs a voltage value (addition output voltage) corresponding to the sum of the light reception levels to the control unit 200, and the amplifier 97 for subtraction outputs a voltage value (subtraction output voltage) corresponding to the difference of the light reception levels to the control unit 200.

In the optical device 100 constituted as described above, the irradiated light B1 emitted from the light source 10 is incident on the left side of the beam splitter 40 through the linear polarizer 20. The measurement light B11 transmitted by this beam splitter 40 is incident on the skin surface of the living body serving as the subject 7 via the condenser lens 50 and penetrates into the subject 7 (living body). The measurement light B11 is then reflected as the reflected light B15 at a predetermined depth position (blood vessel position), and is again incident on the beam splitter 40 via the condenser lens 50. On the other hand, the reference light B13 reflected by the beam splitter 40 is reflected by the reference mirror 60 and is again incident on the beam splitter 40. At this time, the reference light B13 is incident at the incident position of the reflected light B15. The reference light B13 is thereby combined with the reflected light B15. Thereafter, the reflected light B15 is received by the light receiving unit 80 via the orthogonal separation unit 70 and amplified by the amplification unit 90.

The control unit 200 is realized by a microprocessor such as a CPU (Central Processing Unit), a control device such as an ASIC (Application Specific Integrated Circuit, and an arithmetic device, and integrally controls the constituent members of the blood sugar level measurement apparatus 1. This control unit 200 is provided with an optical rotation measurement unit 201 serving as a measurement unit, a reference light path length change control unit 203, and a blood sugar level calculation unit 205. Also, the optical rotation measurement unit 201 has a discrimination unit 202 that discriminates the optical rotation reflecting component of the linear polarization (predetermined polarization) of the reflected light B15. Note that the constituent members constituting the control unit 200 may also be configured by hardware such as dedicated module circuits.

The reference light path length change control unit 203 changes the light path length of the reference light by controlling the reference mirror actuator 65 to move the reference mirror 60 along the X-axis. The optical rotation measurement unit 201 calculates the angle of optical rotation based on the addition output voltage input from the amplifier 95 for addition and the subtraction output voltage input from the amplifier 97 for subtraction. At this time, the discrimination unit 202 analyzes the change in intensity of the reflected light B15 with respect to each of the light path lengths changed to by the reference light path length change control unit 203, and discriminates the polarized light reflection component of linear polarization in the reflected light B15. That is, the discrimination unit 202 specifies a penetration distance l and calculates a light path length L indicating the existence of the optical rotation reflecting component. Using this light path length L, the optical rotation measurement unit 201 calculates the angle of optical rotation. The blood sugar level calculation unit 205 calculates the concentration of glucose based on the light path length L and the angle of optical rotation calculated by the optical rotation measurement unit 201.

The operating unit 300 is realized by various switches such as button switches or dial switches and an input device such as a touch panel, and outputs operation input signals that depend on operation inputs to the control unit 200.

The display unit 400 is realized by a display device such as an LCD (liquid crystal display) or an EL display (electroluminescence display), and displays various screens based on display signals that are input from the control unit 200.

The communication unit 500 is a communication device for transmitting and receiving information to be utilized in the apparatus to and from an external information processor, under the control of the control unit 200. Various methods are applicable as the communication method of the communication unit 500, including a format for establishing a wired connection via a cable compliant with a predetermined communication standard, a format for connecting via an intermediary device that doubles as a charger called a cradle, and a format for establishing a wireless connection utilizing wireless communication.

The storage unit 600 is realized by an IC (Integrated Circuit) memory such as a ROM (Read Only Memory), a flash ROM or a RAM (Random Access Memory), or a storage medium such as a hard disk. The storage unit 600 prestores or temporarily stores a program for operating the blood sugar level measurement apparatus 1 and realizing various functions of the blood sugar level measurement apparatus 1, data that is used during execution of this program, and the like.

Figure 4:
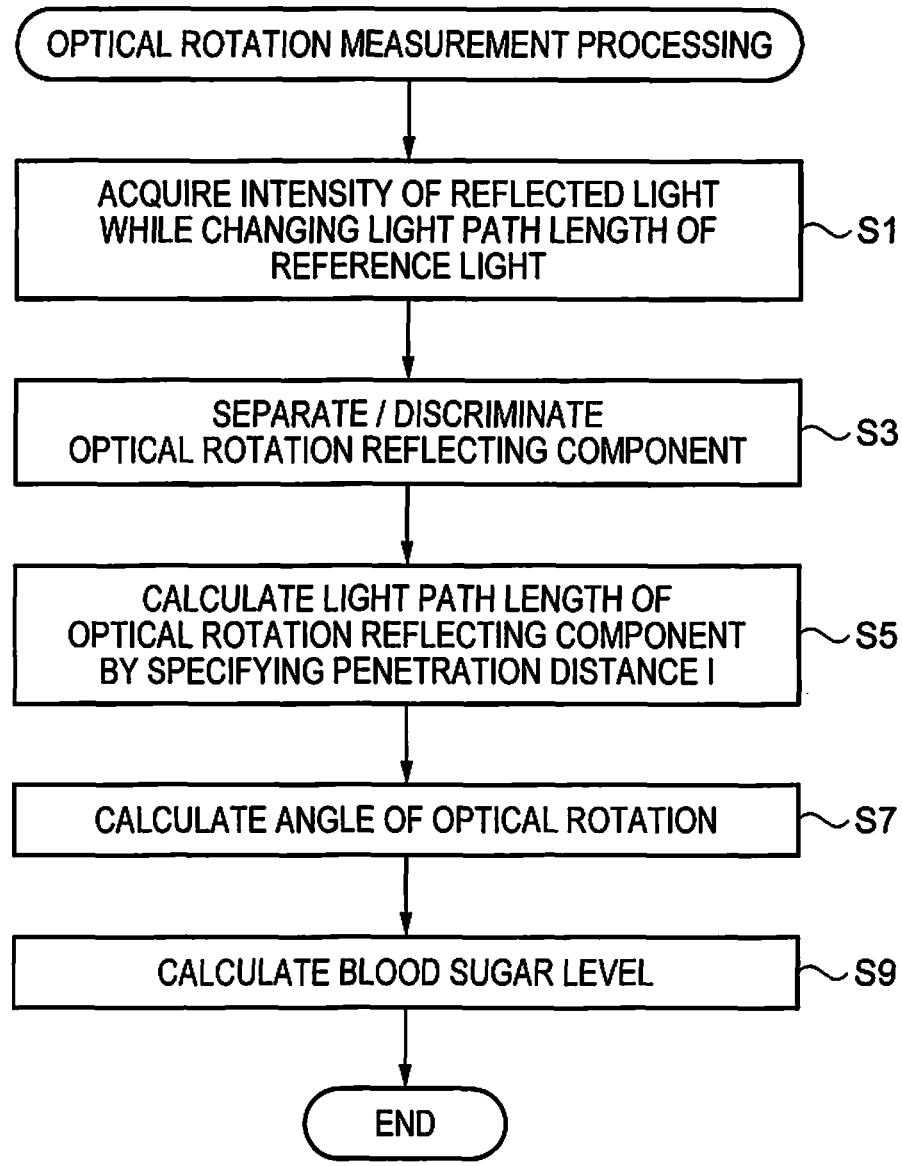
FIG. 4 is a flowchart showing the processing procedure of blood sugar level measurement processing.

This storage unit 600 stores a blood sugar level measurement program 601 for causing the control unit 200 to function as the optical rotation measurement unit 201, the reference light path length change control unit 203 and the blood sugar level calculation unit 205, and performing blood sugar level measurement processing (refer to FIG. 4). In addition, the storage unit 600 stores data such as the addition output voltage value and the subtraction output voltage value input from the amplification unit 90 during the blood sugar level measurement processing, the angle of optical rotation calculated by the optical rotation measurement unit 201, the blood sugar level calculated by the blood sugar level calculation unit 205, and the like as appropriate.

Principles

Figure 2:
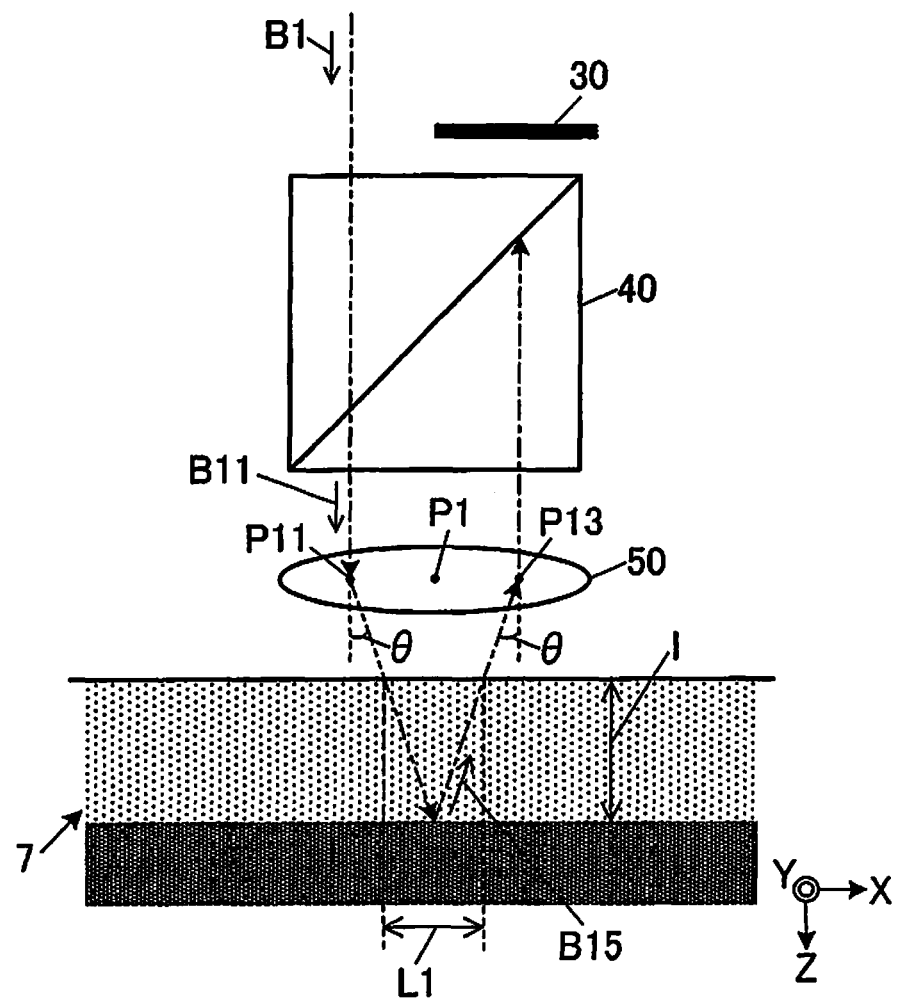
FIG. 2 illustrates the propagation path of light that has penetrated into a subject.

FIG. 2 illustrates the propagation path of light that penetrates into the subject 7. As described above, the measurement light B11 transmitted via the beam splitter 40 is incident on the condenser lens 50 at the measurement light incident position P11, is refracted by the condenser lens 50, and is incident on the surface of the subject 7 at a non-right angle. The measurement light B11 that is thus incident on the subject 7 at a non-right angle penetrates into the subject 7 and is reflected as the reflected light B15 at a depth position of the penetration distance l.

Figure 3A:
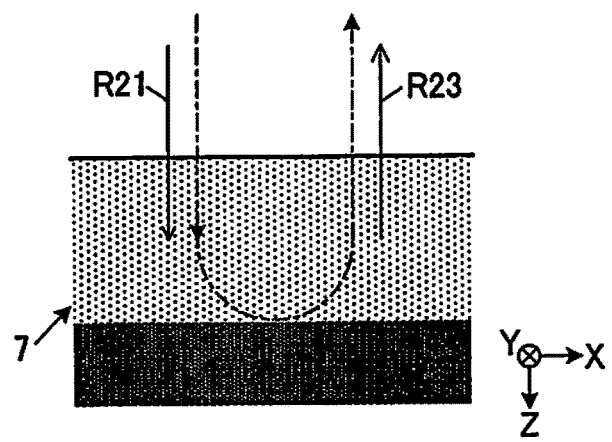
FIGS. 3A to 3C illustrate a problem with conventional reflective optical measurement.
Figure 3B:
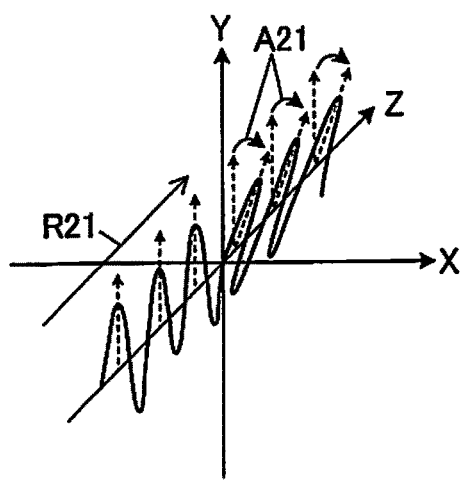
Figure 3C:
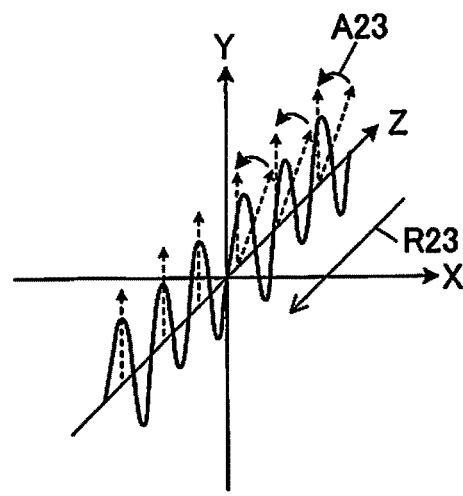

Here, problems with conventional reflective optical measurement will be described, with reference to FIGS. 3A to 3C. FIG. 3A shows propagation paths R21 and R23 of linear polarized light in the case where measurement light (linear polarized light) is incident at a right angle to the subject 7. In order to facilitate understanding, the propagation path R21 and the propagation path R23 are shown as being separate paths for convenience of description, but in practice the paths are the same with opposite propagation directions. Also, FIG. 3B shows optical rotation (rotation of the polarization plane) that occurs in the process of linear polarized light propagating inside the subject 7 in the incident direction thereof, and FIG. 3C shows optical rotation in the process of linear polarized light propagating in the reflection direction.

As shown in FIG. 3A, in the case where the measurement light is incident on the subject 7 at a right angle, the linear polarized light that penetrates into the subject 7 is reflected in an anatomical structure such as blood vessels or subcutaneous fat, and propagates in the opposite direction to the incident direction. Thus, the polarization plane that has rotated as shown by an arrow A21 in FIG. 3B as a result of the linear polarized light passing through an optically active substance in the process of propagating through the subject 7 in the incident direction rotates in the opposite direction to when the linear polarized light was incident as shown by an arrow A23 in FIG. 3C, as a result of the linear polarized light passing through the optically active substance again in the process of propagating in the opposite direction to the incident direction. There is thus a problem in that the optical rotation is cancelled out when the measurement light is incident on the subject 7 perpendicularly, making it difficult to calculate the angle of optical rotation (rotation angle of the polarization plane).

On the other hand, if the measurement light is incident on the subject 7 at a non-right angle, as shown in FIG. 2, the reflected light B15 is reflected in a different direction to the incident direction of the incident light. That is, since the light that propagates inside the subject 7 does not reciprocate on the same path, a situation in which the rotation of the polarization plane is cancelled out can be suppressed, and the angle of optical rotation can be calculated.

Specifically, given that the measurement light B11 is incident on the subject 7 at a non-right angle and is reflected inside the subject 7 in a different direction to the incident direction, the optical rotation resulting from linear polarized light passing through glucose inside the subject 7 (within the living body) is reflected (saved) in the propagation component (orthogonal component) in a direction orthogonal to the Z-axis direction out of the reflected light B15, even though the optical rotation is cancelled out in the propagation component in the Z-axis direction. Accordingly, the angle of optical rotation can be calculated by focusing on this orthogonal component.

An angle of optical rotation φ is proportional to the light path length L of light that propagates inside the subject 7 and a concentration C of the glucose through which the light passes at that time, as shown in the following equation (2). α is a predetermined constant. In the case of focusing on the orthogonal component, a propagation distance L1 in the orthogonal direction shown in FIG. 2 is equivalent to the light path length L, and is represented by 2×penetration distance l×tan θ, where θ is the angle of incidence of the measurement light B11 on the subject 7. Note that although the angle of incidence θ may be set as appropriate, the light path length L can be lengthened the greater the value of θ, thus enabling optical rotation to be measured more accurately.

$$P\phi = L \times C \times \alpha \quad (2)$$

The reflected light B15 that includes the optical rotation reflecting component as the orthogonal component as described above is combined with the reference light B13 in the beam splitter 40. Incidentally, given that the living body serving as the subject 7 is a scattering body, the reflected light B15 is in a greatly scattered state as a result of being propagated inside of the subject 7. Thus, in addition to the abovementioned problem of the optical rotation being cancelled out, there is a problem in that the measurement accuracy of optical rotation is reduced by the noise of the scattered light component.

Here, the reference light B13 is linear polarized light. On the other hand, it is the optical rotation reflecting component included in the reflected light B15 that is to be measured, and this optical rotation reflecting component maintains the polarization plane. Accordingly, when the reference light B13 is combined with the reflected light B15, the reference light B13 interferes with only the optical rotation reflecting component, without interfering with the scattered light component. More specifically, the amplitude of the interference pattern is maximized in the case where the difference between the light path length of the measurement light B11 (light path length from when light passes through the beam splitter 40 as the measurement light B11 until when the light is again incident on the beam splitter 40) and the light path length of the reference light B13 (light path length from when light is reflected by the beam splitter 40 as the reference light B13 until when the light is again incident on the beam splitter 40) is less than or equal to the interference distance Δl of the light source 10.

Accordingly, when measurement is performed while changing the light path length of the reference light B13, the intensity of the reflected light B15 hardly varies and the change thereof is uniform while the difference between the light path length of the measurement light B11 and the light path length of the reference light B13 is greater than the interference distance Δl of the light source 10, whereas the intensity of the reflected light B15 varies greatly and a greatly undulating waveform is obtained when the difference between the light path length of the measurement light B11 and the light path length of the reference light B13 is less than the interference distance Δl. That is, the optical rotation reflecting component can be enhanced so as to enable discrimination. The intensity of the reflected light B15 when the change in intensity is uniform is equivalent to the scattered light component. Accordingly, the scattered light component can, for example, be eliminated by eliminating the intensity of the reflected light B15 that is equivalent to the scattered light component from the intensity of the reflected light B15 when the waveform wave undulates greatly as an offset portion, thus enabling the intensity of the optical rotation reflecting component to be easily separated and discriminated. Also, the penetration distance l shown in FIG. 2 can be specified by acquiring the light path length of the measurement light B11 from the light path length of the reference light B13 when the waveform undulates greatly. For example, given that the interference distance Δl is short at 100 μm or less, the penetration distance l is specified by regarding the light path length of the reference light B13 at the center of the greatly undulating waveform as the light path length of the measurement light B11.

Accordingly, the angle of optical rotation can be calculated based on the intensity of the optical rotation reflecting component that is obtained, and the blood sugar level can be calculated from this angle of optical rotation and the light path length L of the optical rotation reflecting component that is derived from the specified penetration distance l (propagation distance L1 in the orthogonal direction). Here, the angle of optical rotation φ can be calculated using the following equation (3). $V_1+V_2$ is the addition output voltage, $V_1-V_2$ is the subtraction output voltage, and $G_R$ is the gain ratio of the amplification unit 90.

$$\phi[\deg] = 45 - \text{Arccos}\left(\frac{2}{G_R} \cdot \frac{V_1 - V_2}{V_1 + V_2}\right) \quad (3)$$

Flow of Processing

FIG. 4 is a flowchart showing the processing procedure of blood sugar level measurement processing. Note that the processing that is described here can be realized by the control unit 200 reading out the blood sugar level measurement program 601 from the storage unit 600 and executing the read program. The blood sugar level measurement apparatus 1 implements the optical rotation measurement method by performing processing in accordance with the processing procedure shown in FIG. 4.

As shown in FIG. 4, in the blood sugar level measurement processing, the control unit 200 first controls operations of the optical device 100, and acquires the intensity of the reflected light B15 while changing the light path length of the reference light B13 (step S1). Specifically, the control unit 200 performs control for emitting the irradiated light B1 from the light source 10. The reference light path length change control unit 203 in the control unit 200 then controls the reference mirror actuator 65 to move the reference mirror 60 from the end of the movable range at which the light path length of the reference light B13 is shortest to the other end of the movable range at which the light path length of the reference light B13 is longest. The control unit 200 then changes the light path length of the reference light B13 to thus gradually become longer, and acquires the addition output voltage and the subtraction output voltage (i.e., of the corresponding light path length of the reference light B13) at each position of the reference mirror 60.

Next, the optical rotation measurement unit 201 analyzes the change in intensity of the reflected light B15 relative to the change in the light path length of the reference light B13 obtained at step S1, and separates and discriminates the optical rotation reflecting component of linear polarization from the intensity of the reflected light B15 (step S3). The optical rotation measurement unit 201 then calculates the light path length L of the optical rotation reflecting component (propagation distance L1 in the orthogonal direction) by specifying the penetration distance l (step S5).

The optical rotation measurement unit 201 then calculates the angle of optical rotation p in accordance with the above equation (3), based on the intensity of the optical rotation reflecting component discriminated at step S3 (step S7). Thereafter, the blood sugar level calculation unit 205 substitutes the light path length L of the optical rotation reflecting component calculated at step S5 and the angle of optical rotation φ calculated at step S7 into the above equation (1), and obtains the blood sugar level by calculating the concentration C of glucose (step S9).

As described above, the present embodiment enables the measurement light B11 to be incident on the subject 7 from an incident direction that is a non-right angle, and to be reflected in a different direction to the incident direction of the measurement light B11. Also, the light intensity of the optical rotation reflecting component of linear polarization can be separated and discriminated from the reflected light B15, by causing the reference light B13 to combine and interfere with the reflected light B15 while changing the light path length of the reference light B13. In addition, the light path length L of the optical rotation reflecting component can be calculated. Accordingly, the optical rotation can be accurately measured, while suppressing a situation in which optical rotation is cancelled out due to the reflected light being reflected in the same direction as the incident direction of the measurement light. The blood sugar level can be accuracy calculated as a result.

Figure 5:
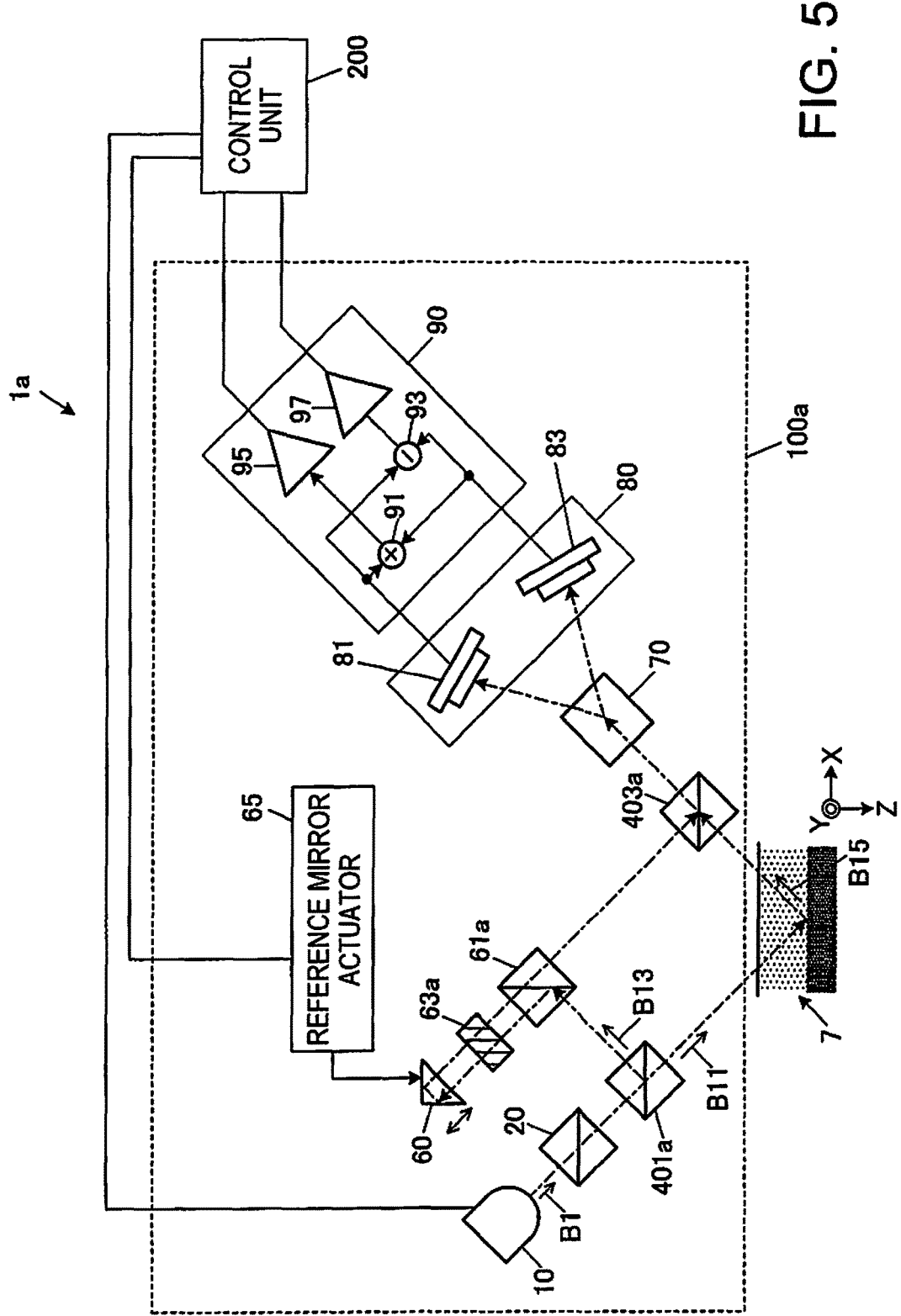
FIG. 5 is a block diagram showing an exemplary configuration of an optical device according to a modification.

Note that the optical device is not limited to the configuration shown in FIG. 1. FIG. 5 shows another exemplary configuration of an optical device 100a. Note that in FIG. 5, the same reference signs are given to configuration that is similar to the above embodiment.

As shown in FIG. 5, the optical device 100a of a blood sugar level measurement apparatus 1a in the present modification is provided with a light source 10, a linear polarizer 20, beam splitters 401a and 403a, a reference mirror 6, a polarized light beam splitter 61a, a 90-degree phase difference plate 63a, an orthogonal separation unit 70, a light receiving unit 80, and an amplification unit 90. The optical elements constituting the constituent members from the linear polarizer 20 to the light receiving unit 80 are disposed at appropriate locations along the light path shown by the dashed-dotted line in FIG. 5 of irradiated light B1 emitted from the light source 10.

In this optical device 100a, the light source 10, the linear polarizer 20 and the beam splitter 401a function as a measurement light irradiation unit, the beam splitter 401a functions as a splitting unit, and the beam splitter 403a functions as a combining unit.

In the present modification, light transmitted via the beam splitter 401a is incident on the subject 7 as the measurement light B11, and the reflected light B15 from the subject 7 is incident on the other beam splitter 403a disposed in the reflection direction thereof. Also, light reflected by the beam splitter 401a is incident on the reference mirror 60 via the polarized light beam splitter 61a and the 90-degree phase difference plate 63a as the reference light B13. The reference light B13 is then caused to combine and interfere with the reflected light B15 by being reflected by the reference mirror 60 that shifts in parallel to the optical axis of the reference light B13, and is incident on the beam splitter 403a via the polarized light beam splitter 61a and the 90-degree phase difference plate 63a.

In the optical device 100a of the present modification, the measurement light B11 is directly incident on the subject 7 at an angle via the beam splitter 401a, and the reflected light B15 from the subject 7 is incident on the beam splitter 403a. In the present modification, in addition to being able to obtain similar effects to the above embodiment, a configuration can be adopted that readily allows the measurement light B11 to be incident on the subject 7a at a large angle of incidence θ compared with the optical device 100 of the above embodiment, thus enabling an improvement in the measurement accuracy of optical rotation to be achieved.

Also, the invention can be widely applied in the case of measuring the angle of optical rotation of an optically active substance. For example, the invention is not limited to the case where the subject is a living body as in the above embodiment, and can also be similarly applied in the case where the subject is blood or the like collected from the person being measured. Also, the invention is not limited to the the case of measuring a person's blood sugar level as in the above embodiment, and can also be similarly applied to a sugar content measurement apparatus that measures the sugar content of fruit, or the like. In the case of applying the invention to a sugar content measurement apparatus, the sugar content of the fruit may be measured with the procedure described with the above embodiment, with the juice of the fruit as the subject, for example.

Also, the blood sugar level measurement apparatus 1 shown in FIG. 1 or the blood sugar level measurement apparatus 1a shown in FIG. 5 can be configured as a wearable device to be used by being attached to a person's body. Alternatively, part of the blood sugar level measurement apparatus 1 or the blood sugar level measurement apparatus 1a, such as the optical device 100 or the optical device 100a, for example, may be configured as a wearable device that is attachable to a person's body.

What is claimed is:

1. An optical rotation measurement method comprising:
   causing a measurement light of a predetermined polarization to be incident on a subject from an incident direction that is a non-right angle to the subject;
   discriminating an optical rotation reflecting component of the predetermined polarization from a reflected light that is reflected in a different direction to the incident direction of the subject;
   measuring an optical rotation based on a result of the discrimination;
   obtaining the measurement light and a reference light from a linear polarized light; and
   causing the reference light to combine and interfere with the reflected light,
   wherein the discrimination includes performing the discrimination using a result of the interference.

2. The optical rotation measurement method according to claim 1, further comprising:
   changing a light path length of the reference light up to where the reference light is combined with the reflected light.

3. The optical rotation measurement method according to claim 2,
   wherein the measurement includes measuring the optical rotation using the light path length.

4. The optical rotation measurement method according to claim 1, further comprising:
   obtaining intensity of the reflected light while changing a light path length of the reference light,
   specifying a penetration distance of the reflected light within the subject, and calculating density of the subject based on the penetration distance and the optical rotation.

5. An optical rotation measurement apparatus comprising:
a measurement light irradiation unit that causes a measurement light of a predetermined polarization to be incident on a subject from an incident direction that is a non-right angle to the subject;
a discrimination unit that discriminates an optical rotation reflecting component of the predetermined polarization from a reflected light that is reflected in a different direction to the incident direction of the subject;
a measurement unit that measures an optical rotation based on a result of the discrimination;
a splitting unit that splits a linear polarized light into the measurement light and a reference light; and
a combining unit that causes the reference light to combine and interfere with the reflected light,
wherein the discrimination unit discriminates the optical rotation reflecting component using a result of the interference.

6. The optical rotation measurement apparatus according to claim 5, further comprising:
a light path length changing mechanism that changes a light path length of the reference light up to where the reference light is combined with the reflected light.

7. The optical rotation measurement apparatus according to claim 6,
wherein the measurement unit measures the optical rotation using the light path length.

8. The optical rotation measurement apparatus according to claim 5,
wherein the splitting unit and the combining unit are configured to share a single beam splitter.

9. The optical rotation measurement apparatus according to claim 5,
wherein the measurement light irradiation unit:
includes a lens unit that serves as an optical front end unit through which incoming and outgoing light passes to and from the subject,
causes the measurement light to be incident on the subject from an incident direction that is a non-right angle to the subject, by shifting an optical axis of the measurement light that passes through the lens unit from a principal point of the lens unit, and
is configured such that the reflected light passes through a position that is symmetrical to the optical axis of the measurement light with the principal point of the lens unit interposed therebetween.

* * * * *